United States Patent
Grauert et al.

[11] Patent Number: 6,124,459
[45] Date of Patent: Sep. 26, 2000

[54] PROCESS FOR PREPARING PHARMACEUTICALLY USEFUL NORBENZOMORPHANE DERIVATIVE

[75] Inventors: Matthias Grauert, Ingelheim; Hanfried Baltes, Woellstein; Juergen Schnaubelt, Biberach an der Riss, all of Germany

[73] Assignee: Boehringer Ingelheim KG, Ingelheim, Germany

[21] Appl. No.: 09/313,001

[22] Filed: May 17, 1999

Related U.S. Application Data

[60] Provisional application No. 60/092,893, Jul. 15, 1998.

[30] Foreign Application Priority Data

May 20, 1998 [DE] Germany ............ 198 22 822

[51] Int. Cl.$^7$ ............ C07D 221/06; C07D 221/26; C07D 221/22

[52] U.S. Cl. ............ 546/97; 546/79

[58] Field of Search ............ 546/79, 97

[56] References Cited

U.S. PATENT DOCUMENTS

| | | | |
|---|---|---|---|
| 3,764,606 | 10/1973 | Akkerman et al. | 546/183 |
| 3,932,422 | 1/1976 | Michne | 546/183 |
| 4,255,579 | 3/1981 | Michne | 548/97 |
| 5,945,535 | 8/1999 | Grauert et al. | 546/97 |

*Primary Examiner*—Alan L. Rotman
*Assistant Examiner*—Rita Desai
*Attorney, Agent, or Firm*—R. P. Raymond; A. R. Stempel; M-E M. Devlin

[57] ABSTRACT

The present invention relates to a new process for preparing norbenzomorphane derivatives of general formula 1

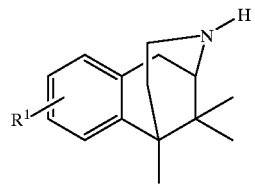

15 Claims, No Drawings

PROCESS FOR PREPARING PHARMACEUTICALLY USEFUL NORBENZOMORPHANE DERIVATIVE

This application claims benefit under U.S.C. § 119 (e) of U.S. Provisional Application No. 60/092,893, filed Jul. 15, 1998.

The present invention relates to a new process for preparing norbenzomorphane derivatives of general formula 1 (Figures 1a and 1b show the corresponding stereoisomers, the text discusses only the preparation of the R-enantiomers—the S-enantiomers can be prepared analogously):

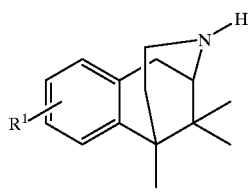

1

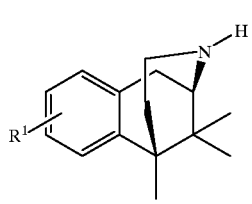

1a

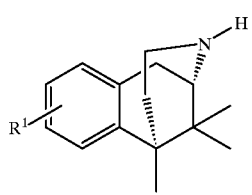

1b wherein $R^1$ may denote H, $C_1$–$C_8$-alkyl, $C_1$–$C_8$-alkoxy, hydroxy or halogen.

Unless specifically stated otherwise, the general definitions are used in the following sense:

$C_{1-8}$-alkyl generally denotes a branched or unbranched hydrocarbon group having 1 to 8 carbon atom(s) which may optionally be substituted with one or more halogen atom(s)—preferably fluorine—which may be the same as one another or different. The following hydrocarbon groups are mentioned by way of example:

methyl, ethyl, propyl, 1-methylethyl (isopropyl), butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2,-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Unless stated otherwise, lower alkyl groups having 1 to 3 carbon atoms, such as methyl, ethyl, propyl and isopropyl, are preferred.

$C_{1-8}$-alkoxy generally denotes a branched or unbranched $C_{1-8}$-hydrocarbon group bound via an oxygen, which may optionally be substituted with one or more halogen atom(s)—preferably fluorine—which may be the same as or different from one another. The following hydrocarbon groups are mentioned by way of example:

methoxy, ethoxy, propoxy, 1-methylethyl (isopropyl), butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2,-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Unless stated otherwise, lower alkoxy groups having 1 to 3 carbon atoms, such as methoxy, ethoxy, propoxy and isopropoxy, are preferred.

For the purposes of the present invention, halogen denotes fluorine, chlorine, bromine and iodine, of which fluorine and chlorine are preferred as substituents. Bromine and chlorine, particularly chlorine, are preferred as anions in aluminium compounds.

The process can be used to synthesise the racemic compounds and to synthesise the corresponding enantiomerically pure compounds. Compared with the process described in published German application 195 28 472 the process according to the invention has the advantage that it eliminates two steps, namely the introduction of the N-formyl protecting group and its subsequent removal. Moreover, in the case of the 4'-methoxy-substituted norbenzomorphane ($R^1$=4'-OMe), which is a valuable intermediate for pharmaceutically active norbenzomorphane derivatives, the yields of the desired compound are significantly better.

The prior art mentioned hereinbefore describes a process in which corresponding 4-methylene-piperidine derivatives 2 are cyclised, after the introduction of an N-formyl protecting group—3—to obtain the corresponding benzomorphane derivatives 4. However, in order to obtain the corresponding norbenzomorphanes 5, the formyl protecting group has to be cleaved again in a further step.

Subsequently, if desired, the substituent $R^2$ may be modified in a manner known per se to obtain $R^1$ according to the desired compound 1. Thus, if $R^2$ denotes an alkoxy group—such as e.g. methoxy, ethoxy, n-propoxy or iso-propoxy—the corresponding hydroxy compound ($R^1$=OH) may be generated by ether splitting—e.g. by reacting with a hydrohalic acid such as HBr.

It has now been found that, surprisingly, with the process according to the invention, there is no need to introduce a formyl protecting group. According to the invention the piperidine derivative 2 in the protonated form can be cyclised directly with $AlCl_3$ to obtain the benzomorphane derivative 5. The synthesis is illustrated in diagram 1 for the corresponding 1R-enantiomers. However, it may also be carried out analogously with the corresponding 1S-enantiomers or with the racemic starting compounds.

Diagram 1:

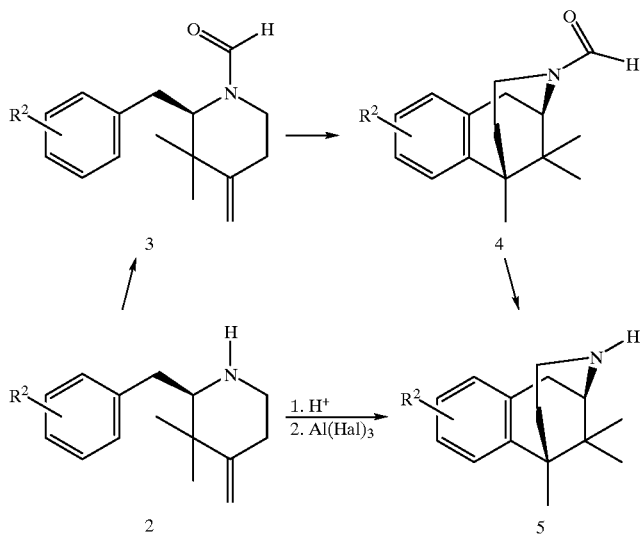

Thus, using the process described in the prior art, the desired benzomorphane derivative is obtained in only a 20% yield, in the case of the 2-(2-methoxyphenyl)methyl-3,3-dimethyl-4-methylene-piperidine 2a ($R^2$=2-OMe). The new process, on the other hand, yields the desired benzomorphane derivative of type 5—with $R^2$=OCH$_3$ in this instance—in an isolated yield of over 80%.

Variations in the experimental conditions (Table 1) show that for successful cyclisation the 4-methylene-piperidine 2 has only to be first converted into a salt, as cyclisation of the free base predominantly yields decomposition products of an unknown nature.

The process according to the invention is suitably carried out in a reaction medium. Suitable reaction media include, in particular, halogenated aliphatic or aromatic hydrocarbons or else also acid amides, of which mono- or polychlorinated alkanes having 1 to 3 C-atoms or chlorinated benzene (-derivatives) or acid amides of $C_{1-3}$-carboxylic acids are particularly preferred. Most particularly preferred are dichloromethane (methylene chloride), 1,2-dichloroethane, chlorobenzene and dimethylacetamide. However, mixtures of the above solvents may also be used.

The reaction temperature for the reaction according to the invention is not critical within wide limits. It will depend primarily on the reactivity of the reactants, whilst the upper limit is set by the boiling point of the solvent—unless the reaction is carried out in an autoclave. Thus, the reaction according to the invention can be carried out within a temperature range of from 0 to 150° C. depending on the solvent used. A range from 20 to 100° C. is preferred, whilst a range from 40 to 70° C. is particularly preferred.

The quantity of aluminium (III) halide used—preferably aluminium tribromide and most preferably aluminium trichloride—is also variable within wide limits. It is typically within a range from 2 to 12 equivalents of aluminium chloride, based on the educt. A ratio in the range from 3 to 10 equivalents is particularly preferred, whilst a ratio in the range from 3 to 5 equivalents is most particularly preferred.

The salt form used is also not critical in terms of dvantageously carrying out the reaction according to the invention. It is preferable to use the salts of the piperidine derivatives of type 2 with inorganic acids—particularly mineral acids. The—neutral—salts with hydrohalic acids or sulphuric acid are preferred. Apart from neutral sulphates (abbreviated to "SU1" in Table 1) it is most preferable to use hydrochlorides (Cl) or hydrobromides (Br).

The invention described hereinbefore is also illustrated by the process described in the following Examples. Various other embodiments of the process according to the invention will become apparent to the skilled person from the description provided. However, it is expressly pointed out that the Examples and the specification are intended solely as an illustration and should not be regarded as restricting the invention.

EXAMPLES

Example 1

(−)-4'-methoxy-5,9,9-trimethyl-6,7-benzomorphane-tartrate ((−)-5aTA)

4.9 g (20 mmol) of (+)-2-(2-methoxyphenyl)methyl-3,3-dimethyl-4-methylene-piperidine (2a) are dissolved in 20 ml of acetone and 1 g of conc. sulphuric acid are added. The crystals precipitated are suction filtered and suspended in 6 ml of dichloromethane[1],[2]. 9 g (68 mmol) of AlCl$_3$ are added, with cooling, at 10–20° C. A clear solution is formed which is subsequently boiled for 2 h (internal temperature 46° C.). The reddish-brown reaction mixture is cooled to ambient temperature, diluted with 25 ml of dichloromethane and added to about 100 g of ice. 100 ml of 20% NaOH are added dropwise thereto with cooling at 20–25° C., then the organic phase is separated off and the aqueous phase is extracted with 25 ml of dichloromethane. The combined organic extracts are dried over magnesium sulphate and the solvent is distilled off in vacuo. The residue is taken up in 10 ml methanol and 3.1 g of L-(+)-tartaric acid[3] in 2 ml H$_2$O are added. The mixture is left in an ice bath for 10 minutes to crystallise out, diluted with about 40 ml of acetone and suction filtered.

Yield: 6.5 g (82.3%), melting point: 236° C.

1) The use of 1,2-dichloroethane as an alternative yields 78% benzomorphane after the reversed addition of AlCl$_3$ and after 30 min. at 55° C.
2) The reaction in dichloromethane at 55° C. under pressure yields the benzomorphane in an 82% yield after 1.5 hours.
3) Alternatively, 62% HBr can be used for the crystallisation. The corresponding hydrobromide is isolated in a 77% yield.

TABLE 1

| salt | solvent | AlCl$_3$ | temperature | time | yield |
|---|---|---|---|---|---|
| Cl | chlorobenzene | 4.0 eq | 90° C. | 15' | 58.0% |
| Cl | chlorobenzene | 4.0 eq | 75–80° C. | 2 h | 61.7% |
| Cl | CH$_2$Cl$_2$ | 4.0 eq | 20–25° C. | 48 h | 44.4% |
| Cl | CH$_2$Cl$_2$ | 3.2 eq | 20–25° C. | 64 h | 54.4% |
| Cl | C$_2$H$_4$Cl$_2$ | 4.0 eq | 55–60° C. | 6 h | 42.0% |
| Cl | C$_2$H$_4$Cl$_2$ | 3.2 eq | 42° C. | 5 h | 78.8% |
| Br | chlorobenzene | 4.0 eq | 60° C. | 2 h | 63.6% |
| SU1 | C$_2$H$_4$Cl$_2$ | 3.4 eq | 60–65° C. | 2 h | 85.3% |
| SU1 | C$_2$H$_4$Cl$_2$ | 3.4 eq | 55–60° C. | 30' | 91.1% |
| SU1 | C$_2$H$_4$Cl$_2$ | 3.4 eq | 50–55° C. | 30' | 90.5% |
| SU1 | CH$_2$Cl$_2$ | 3.4 eq | 55° C. autoclave | 1.5 h | 82.0% |
| SU1 | CH$_2$Cl$_2$ | 3.4 eq | 46–47° C. slurry | 2 h | 90.3% |
| SU1 | DMAA | 8.0 eq | 80–90° C. | 3 h | 60% |

Example 2

(−)-3'-Methoxy-5,9,9-trimethyl-6,7-benzomorphane-tartrate ((−)-5bTA)

8.6 g (35 mmol) of (+)-2-(3-methoxyphenyl)methyl-3,3-dimethyl-4-methylene-piperidine (2b) are dissolved in 35 ml of acetone and 1.8 g of conc. sulphuric acid are added. The precipitated crystals are suction filtered and suspended in 10.5 ml of 1,2-dichloroethane. To this are added 16 g (120 mmol) of AlCl$_3$, whilst cooling to 20–30° C. The mixture is quickly heated to 55–70° C. After 30 min. it is left to cool to ambient temperature, diluted with 100 ml of dichloromethane and 200 g of ice water are added. Whilst cooling to 20–25° C., 300 ml of 20% NaOH are added dropwise thereto, the organic phase is then separated off and the aqueous phase is extracted with 150 ml of dichloromethane. The combined organic extracts are dried over magnesium sulphate and the solvent is distilled off in vacuo. The residue is taken up in 20 ml methanol and 5.4 g of L-(+)-tartaric acid in 3 ml of H$_2$O are added. The mixture is left in an ice bath for 10 minutes to crystallise out, diluted with about 40 ml of acetone and suction filtered.

Yield: 10.9 g (79%), melting point: 186° C.

What is claimed is:

1. A process for preparing an R- or S-norbenzomorphane of formula 1

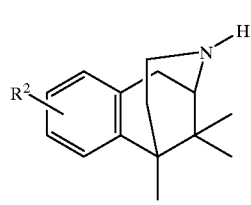

wherein

R$^1$ is H, C$_{1-8}$ alkoxy, hydroxy or halogen, which comprises the steps of converting a 4-methylene-piperidine derivative of formula 2

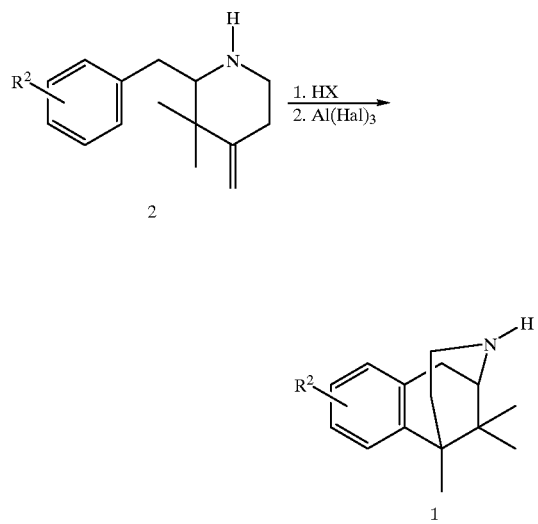

(where R$^2$ is R$^1$)

with an acid into the corresponding acid addition salt, reacting said corresponding acid addition salt in a reaction medium with an aluminum (III) halide at a temperature in the range from about 0° C. to about 150° C., and isolating the R- or S-norbenzomorphane of formula 1.

2. The process according to claim 1 wherein the aluminum (III) halide is aluminum tribromide or aluminum trichloride.

3. The process according to claim 1, wherein the reaction medium is a mono- or polychlorinated alkane having 1 to 3 carbon atoms, a chlorinated benzene or benzene derivative or an amide of a C1–3-carboxylic acid or a mixture of such.

4. The process according to claim 1, where the reaction medium is dichloromethane, 1,2-dichloroethane, chlorobenzene or dimethylacetamide or a mixture of such.

5. The process according to claim 1, wherein the reaction is carried out at a temperature in the range from about 20 to about 150° C.

6. The process according to claim 4, wherein the reaction is carried out at a temperature in the range from about 40 to about 70° C.

7. The process according to claim 1, wherein about 2 to about 12 equivalents of aluminum (III) halide are used, based on the educt.

8. The process according to claim 7, wherein about 3 to about 10 equivalents of aluminum (III) halide are used, based on the educt.

9. The process according to claim 8, wherein about 3 to about 5 equivalents of aluminum (III) bromide or aluminum (III) chloride are used, based on the educt.

10. The process according to claim 1, where (+)-2-(3-methoxyphenyl)methyl-3,3-dimethyl-4-methylene-piperidine is used as the piperidine derivative.

11. The process according to claim 1, where (−)-2-(3-methoxypheneyl)methyl-3,3-dimethyl-4-methylene-piperidine is used as the piperidine derivative.

12. The process according to claim 1, where the piperidine derivative is used in the form of an addition salt with a mineral acid.

13. The process according to claim 12, wherein the piperidine derivative used is in the form of an addition salt with a hydrohalic acid or sulphuric acid.

14. The process according to claim 13, wherein the piperidine derivative used is in the form of an addition salt with hydrochloric or hydrobromic acid.

15. The method as recited in claim 1 where $R^2$ is alkoxy further comprising the step of converting the alkoxy to hydroxy through ether splitting by reacting with a hydrohalic acid.

* * * * *

UNITED STATES PATENT AND TRADEMARK OFFICE
CERTIFICATE OF CORRECTION

PATENT NO. : 6,124,459
DATED : September 26, 2000
INVENTOR(S) : Grauert, M. et al It is certified that error appears in the above-identified patent and that said Letters Patent is hereby corrected as shown below:

Title page item [73], change Boehringer Ingelheim KG to -- Boehringer Ingelheim Pharma KG --.

Signed and Sealed this

Ninth Day of January, 2001

Attest:

Q. TODD DICKINSON

*Attesting Officer*         *Commissioner of Patents and Trademarks*